United States Patent [19]
Julian et al.

[11] Patent Number: 5,500,216
[45] Date of Patent: Mar. 19, 1996

[54] TOPICAL HYDROPHOBIC COMPOSITION AND METHOD

[76] Inventors: Jorge V. Julian, 7340 Bequette Ave., Pico Rivera, Calif. 90660; John A. Garruto, 110 Paseo Marguerita, Vista, Calif. 92084

[21] Appl. No.: 79,333

[22] Filed: Jun. 18, 1993

[51] Int. Cl.$^6$ .................................................. A61K 31/74
[52] U.S. Cl. ..................... 424/401; 424/78.03; 424/489
[58] Field of Search ............................................... 424/401

[56] References Cited

U.S. PATENT DOCUMENTS 3,023,181  2/1962  Grotenhuis .............................. 260/29.2
5,223,559  6/1993  Arraudeau et al. ...................... 424/401
5,229,121  7/1993  Razzano et al. ......................... 424/401

*Primary Examiner*—Thurman K. Page
*Assistant Examiner*—William E. Benston, Jr.

[57] ABSTRACT

Drag is reduced during swimming by topically applying a film of rough particles of hydrophobic metal oxide such as organo silicon modified silicon oxide particles to certain skin surfaces of the swimmer. A uniform suspension of a long acting composition is formed by a mixture of 2 hydrophobic metal oxides in vaporizable liquid carrier such as ethanol containing a vaporizable plasticizer such as propylene glycol in which the amount of the larger hydrophobic metal oxide particles in the mixture predominates over the amount of smaller particles of hydrophobic metal oxide.

15 Claims, No Drawings

TOPICAL HYDROPHOBIC COMPOSITION AND METHOD

DESCRIPTION

1. Technical Field

The present invention relates to a hydrophobic composition to be topically applied to skin and, more particularly, this invention relates to a hydrophobic composition for reducing drag during swimming.

2. Background of the Invention

Individuals who participate in water sports such as competition swimmers and water polo players apply materials such as mineral oil, wintergreen oil, vaseline, etc. to certain body surfaces in order to reduce drag. This reduces friction of the body of the swimmer as he moves through the water and increases swimming speed. The oily or greasy substances that are in use can damage pool filters and motors and are not readily removed from water by filtration. The oily and greasy materials are applied as a thick coat or film since these materials tend to wash off by the action of the water current as one swims through the water. The film closes skin pores interfering with sweating and respiration of the skin. The oily or greasy materials can spill or drip during application causing a hazardous condition in the locker room or on the deck surfaces adjacent to a swimming pool. Furthermore, the hydrocarbon based oils and greases are difficult to remove from the skin by soap and water. They require scrubbing or brushing to remove the materials from the skin.

The oils or greases now in use do reduce drag. However, drag could be further reduced if the skin surfaces could be rendered more hydrophobic.

STATEMENT OF THE INVENTION

A composition with extremely high hydrophobicity is provided by the invention. Swimmers topically applying the superhydrophobic product of the invention to their skin find that water drag is reduced and speed is increased. The hydrophobic composition of the invention is easily filtered out of water recirculating in a pool system. It is not slippery if spilled and is readily removed from skin with soap and water. However, the composition stays on the skin much better than oils while the swimmer is in the water. Water does not frictionally engage the superhydrophobic material. Water forms spherical beads which readily roll off the film. Since the interface with water does not from a cohesive film, there is less adhesive force applied against the superhydrophobic film by water. Once the composition is applied to the skin, water rolls off the skin as spherical droplets.

The composition of the invention has been tested and compared with oily drag reducing products. Preliminary results indicate it significantly outperforms the oily product in reducing drag and increasing speed of swimming. Preliminary tests also confirm that the composition of the water is hypo-allergenic causing no irritation or inflammation of the skin.

Hydrophobicized metal oxide particles are known to have hydrophobic properties. Due to their small size and large surface area they also are used as fillers or additives to provide free flow or thickening to products such as printing inks, greases and fire-extinguishing powders. They have been used in coating formulations to coat paper, textiles, wood, concrete and plastic surfaces.

The composition of the invention is a uniform suspension of hydrophobicized metal oxide particles, particularly hydrophobicized silicon dioxide particles in a pharmacologically acceptable fluid carrier. The carrier can be a pressurized, liquefied propellant gas such as isobutane or a vaporized liquid carrier such as an alcohol. The hydrophobicized particles act to repel water in two ways. The particles are prepared by reacting residual silanol groups on the surface with organic materials. These materials react to form a sheath or coating of hydrophobic hydrocarbon groups on the surface of rough particles. When the particles are applied to the skin they form a discontinuous particle coating. A vast number of tiny particles are deposited. A monolayer is estimated to contain $2\times10^{12}$ particles per square centimeter. The microrough surface supports the water droplet on a plurality of point projections decreasing the contact angle. This phenomena combined with the hydrophobic shell provides very little adhesive force for the water, a property known as superhydrophobicity. The water droplets aggregate into separate spheres.

The preferred form for formulating the hydrophobic film forming composition of the invention is a lotion in which the hydrophobic metal oxides are dispersed in a volatile liquid carrier. Pressurized formulations are expensive to package and utilize flammable propellants such as isobutane. The liquid carrier is only required to maintain the powder in dispersion and to provide lubricity and fluidity as the composition is applied to the skin. After application, the carrier evaporates from body heat and leaves a discontinuous film of hydrophobic metal oxide on the skin.

Aerosol dispersions of hydrophobicized silicone particles are now used for the opposite purpose - to keep palm surfaces dry in sports such as weight lifting, bowling and the like. These products can be used in the water sports method of the invention.

Another aspect of the invention is an improvement in which the hydrophobicized metal oxide particles are dispersed in a liquid carrier. The particles are found to settle. However, it has also been discovered in accordance with the invention that the dispersion of the hydrophobicized metal oxide particles can be stabilized if particles of two different size ranges are utilized.

These and many other features and attendant advantages of the invention will become apparent as the invention becomes better understood by reference to the following detailed description.

DETAILED DESCRIPTION OF THE INVENTION

The hydrophobic composition of the invention contains from 2–20% by weight, usually 5–10% by weight of hydrophobic metal oxide particles dispersed in a fluid carrier, preferably 60–90% by weight of a liquid vaporizable under ambient conditions. The carrier can be water, an alkanol containing 1–6 carbon atoms or mixtures thereof. In order to provide more of a lotion or gel feel, the composition may optionally contain from 1 to 10% by weight of a hypoallergenic plasticizer such as a polyol containing from 2–8 carbon atoms such as ethylene glycol, propylene glycol, glycerol or dimers, trimers and liquid polymers thereof or alkoxylated derivatives thereof such as methoxylated polyols. The preferred plasticizer is propylene glycol since it provides a lubricating feel when applying the composition to the skin but evaporates within a few minutes after application.

Synthesis of hydrophobic metal oxides by reaction of metal oxides and metalloid oxides, particularly colloidal silicas, with various organosilicon compounds has been rather extensively developed. Various organosilicon compounds bearing at least one functional moiety per molecule can be reacted through said functional moiety with the hydroxyl groups existing on the surface of the metal or metalloid oxides. The resulting reaction product is characterized as a metal oxide or metalloid oxide having chemically bonded to the surface thereof organosilicon groups represented generally by the formula:

$$_eO-MR_aX_b$$

where e represents the oxide surface; O is oxygen; M is a metal or metalloid such as silicon, each R is any alkyl, aryl, arylalkyl, alkoxy or aryloxy group, a is a number from 1 through 3, X is any halogen or hydroxy group, b is a number from 0 through 2, and a+b=3.

The organosilicon groups are introduced onto the surface of the metallic oxide in an amount sufficient to render the surface of the metal oxide hydrophobic. Generally, at least 50% of the available oxygen groups on the surface such as silanol groups are converted, typically about 70%. Hydrophobic, pyrogenic silica can be produced in accordance with the teachings of U.S. Pat. No. 3,393,155 or other patents such as U.S. Pat. Nos. 2,510,661, 2,589,705, 2,705,206 2,705,222 and 3,023,181.

In preparing the dispersion of aqueous liquid in fine solid particulates for use in the present invention, in addition to or in place of the hydrophobic pyrogenic silicas used in U.S. Pat. No. 3,393,155 other strongly, hydrophobic metallic oxides having an average equivalent spherical diameter of less than about 100 millimicrons, typically from 1 to 20 millimicrons, can also be used. For example, other finely divided oxides such as aluminas, titanias, ziconias, vanadium oxides, iron oxides or mixed oxides with or without silica can form the basic oxide particles whether produced pyrogenically or otherwise, e.g., by wet precipitation techniques. Also, wet precipitated silicas such as those produced by acidification or neutralization of aqueous alkali metal silicate solutions make ideal starting materials when available in particulate form of the desired fineness. For example, U.S. Pat. Nos. 2,865,777, 2,900,348, 2,913,419, 2,995,422, 3,010,791, 3034,913, 3,172,726, 3,208,823 and 3,250,594 describe a few of the many different techniques for precipitating particulate silicas from aqueous medium in a form which is sufficiently non-sticky and non-gelatinous to be washed, filtered, dried and subdivided to colloidal powder form.

Specific examples of organosilicon compounds which are often reacted with colloidal metallic oxides to form surface structures like those described above are: organohalosilanes such as $(CH_3)_3SiCl$, $(CH_2)_2SiBr_2$, $(CH_3)_2SiCl_2$ and $(C_4H_9)SiCl$; organosilylamines such as $(CH_3O)_3Si(CH_2)_3$-$NH(CH_2)_2NH_2$ and $(CH_3O)_2(CH_3)SiCH_2CH(CH_3)$-$CH_2NHCH_2CH_2NH_2$; organodisilazanes such as $(CH_3)_3SiNHSi(CH_3)_3$ and $(C_4H_9)_3$-$SiNHSi(C_4H_9)_3$, etc. In most cases, the surface treatments must be sufficient to attach organo groups totaling at least 0.5 percent by weight based on the dry weight of the metallic oxide particles treated. In many cases, especially with the most preferred high surface area oxides, the concentration of organo groups thereon will equal 2 percent or more by weight.

The composition is used by applying a wet film of the composition to the surfaces of the swimmer where drag reduction is desired such as shoulders, outside surfaces of the arm, etc. The film is allowed to dry on the skin to form a discontinuous film of hydrophobic metal particles. The surfaces where friction is desired are purposely not coated, such as the palms of the hands and the inside surfaces of the forearm. The exact surfaces to be covered depends on the stroke to be utilized by the swimmer.

After the competition is completed, the film of hydrophobic metal oxide is readily removed from the skin with soap and water without any need to vigorously brush or scrub the film.

The preferred hydrophobic metal oxides are fumed silicon oxide having a surface area from 10–800 sq. meter per gram, preferably from 50 to 300 sq. meters per gram. Compositions have been prepared and tested with CAB-O-SIL TS-530 and CAB-O-SIL 720. TS-530 is prepared by reacting hexamethyldisilizane with the surface moisture on high purity silica. The silizane hydrolyzes into 2 trimethyl silyl groups and ammonia. The trimethyl silyl groups react with surface hydroxyl groups to form a hydrophobic surface as represented by the following formula:

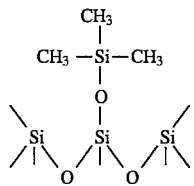

TS-530 has a BET surface area of 200±40 m$^2$/g and a carbon content of at least 3.4 % by weight and a bulk density of 4.51 lbs/ft$^3$.

TS-720 is prepared by reacting high purity silica with dimethyl silicone fluid to form a surface in which polydimethyl siloxane polymer units are attached to the surface of the particles as follows:

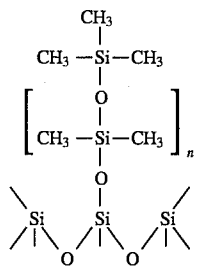

TS-720 has a BET surface area of 100±20 m$^2$/g, a minimum carbon content of 4.5% by weight and a bulk density of 3.0 lbs/ft$^3$.

Compositions were formulated from TS-530 and TS-720 powders as follows:

EXAMPLE 1

| Ingredient | Amount, % by weight |
|---|---|
| Denatured Ethyl Alcohol | 87.13 |
| CAB-O-SIL 530 | 6.8 |
| Propylene glycol | 3.25 |
| Silicone | .02 |
| | Does not add up to 100% |

EXAMPLE 2

| Ingredient | Amount, % by weight |
|---|---|
| Denatured Ethyl Alcohol | 87.13 |

-continued

| Ingredient | Amount, % by weight |
| --- | --- |
| CAB-O-SIL 720 | 6.8 |
| Propylene glycol | 3.25 |
| Silicone | .02 |

EXAMPLE 3

| Ingredient | Amount, % by weight |
| --- | --- |
| Denatured Ethyl Alcohol | 87.13 |
| CAB-O-SIL 530 | 1.8 |
| CAB-O-SIL 720 | 5.0 |
| Propylene glycol | 3.25 |

The compositions of Examples 1–3 were tested by swimmers and all displayed excellent hydrophobic and drag reduction properties. The subject testing the products stated that the film of the composition felt smoother than shaving in terms of feel for the water. He also reported that he felt he slipped through the water better than when he used oily drag reducing products. Preliminary testing of the products shows good hypo-allergenic characteristics.

The formulation of Example 1 did not remain on the skin as long as the compositions of Examples 2 and 3 but had excellent stability in suspension. The composition of Example 2 stayed on the skin longer but tended to settle while in the container. The composition of Example 3 stays in suspension well and has best stability on the subject. The preferred composition contains 0.5 to 5% of the TS-530 and 2–10% of the TS-720 with the ratio of amounts of TS-720/TS-530 exceeding 1.

The composition of Example 3 was tested according to the following protocol:

Passive Drag Measurements

All passive drag measurements were made using a load cell interfaced with a computer. Drag measurements were made at four water velocities (1.0 m/s, 1.5 m/s, 2.0 m/s and 2.4 m/s): One subject was towed in a streamlined position without and with the composition of Example 3. Three trials at four different speeds (1.0 m/s, 1.5 m/s, 2.0 m/s, 2.4 m/s) were averaged without and with the composition of Example 3.

| PASSIVE DRAG VALUES WITH AND WITHOUT COMPOSITION OF EXAMPLE 3 | | |
| --- | --- | --- |
| Velocity | Without | With |
| 1.0 m/s | 4.65 ± 0.13 | 4.80 ± 0.32 |
| 1.5 m/s | 12.15 ± 0.18 | 10.82 ± 0.53 |
| 2.0 m/s | 22.65 ± 0.48 | 20.63 ± 1.22 |
| 2.4 m/s | 38.35 ± 2.25 | 36.98 ± 2.55 |

There were decreases in passive drag at velocities above 1.0 m/s when using the composition of the invention. The percent decreases at the different velocities above 1.0 m/s were:

| 1.5 m/s | 10.95% |
| --- | --- |
| 2.0 m/s | 8.92% |
| 2.4 m/s | 3.57% |

The composition of the invention contributes to increase in speed of swimming since skin covered with a film of the composition exhibits less drag. Water literally rolls off skin coated with a film of the hydrophobic particles. The hydrophobic properties are so high that the coated skin does not get wet. The high water repellency decreases slow swimming. The reduction in drag permits a swimmer to swim at a certain speed with less effort which can contribute to increased endurance for long distance swimmers. There are no oils to damage pool equipment. Any dislodged particles are readily filtered out in the pool filter. The film washes off with soap and water. The composition can also be used to increase friction of the palm in non-water sports such as weight lifting, gymnastics, bowling, archery, etc.

It is to be realized that only preferred embodiments of the invention have been described and that numerous substitutions, modifications and alterations are permissible without departing from the spirit and scope of the invention as defined in the following claims.

We claim:

1. A method of reducing drag of a swimmer relative to water comprising the steps of:

before swimming, topically applying to body surfaces of a swimmer a dispersion of particles of hydrophobic metal oxide in a pharmacologically acceptable fluid carrier; and removing the carrier to form a film of hydrophobic metal oxide particles on said surfaces.

2. A method according to claim 1 wherein the metal oxide is a silicon dioxide treated with hexamethyldisilazane or silicon dioxide treated with dimethyldichlorosilane or silicon dioxide treated with a polydimethyl siloxane polymer.

3. A method according to claim 2 wherein the carrier is a liquid vaporizable under ambient conditions, The carrier can be water, an alkanol containing 1–6 carbon atoms or mixtures thereof.

4. A method according to claim 3 wherein the liquid contains (a minor amount of a plasticizer) from 1–10% by weight of hypo-allergenic plasticizer such as a polyol containing from 2–8 carbon atoms such as ethylene glycol, propylene glycol, glycerol, or dimers, trimers and liquid polymers thereof or alkoxylated derivatives thereof such as methoxylated polyols.

5. A method according to claim 3 in which the particles have a rough surface.

6. A method according to claim 5 in which the particles are present in the dispersion in an amount of from 2–20% by weight and the surface of the particles contain silanol groups connected to organosilicon moieties which provide hydrophobic properties to the particles.

7. A method according to claim 6 in which at least 70% of the surface silanol groups are connected to organosilicon groups.

8. A method according to claim 7 in which the organo groups of the organosilicon moieties are selected from alkyl, aryl, arylalkyl, alkoxy or aryloxy containing from 1 to 20 carbon atoms.

9. A method according to claim 1 in which the metal oxides have a surface area from 10–800 sq. meter per gram.

10. A superhydrophobic, lotion composition for application to the skin of users comprising:

a uniform dispersion of a hydrophobic silicon oxide in a pharmacologically acceptable liquid carrier, vaporizable at ambient conditions and including a minor amount of a plasticizer.

11. A composition according to claim 10 in which the hydrophobic metal oxide is present in an amount from 2–20% by weight.

12. A composition according to claims 11 in which the hydrophobic metal oxide is a mixture of a minor amount of a first hydrophobic silicon oxide and a minor amount of a second hydrophobic silicon oxide having a surface area at least 1.5 times the surface area of the first hydrophobic metal oxide.

13. A composition according to claim 12 in which the liquid carrier is a lower alkanol present in an amount form 60–90% by weight and the plasticizer is a liquid polyol present in an amount from 1 to 10% by weight.

14. A composition according to claim 13 in which the alkanol is ethanol and the polyol is propylene glycol.

15. A composition according to claim 14 in which the first hydrophobic metal oxide contains polydimethyl siloxane polymeric groups on its surface and the second hydrophobic metal oxide contains trimethyl silyl groups on its surface.

* * * * *